(12) United States Patent
Sahakian et al.

(10) Patent No.: US 10,835,311 B2
(45) Date of Patent: Nov. 17, 2020

(54) ELECTROPORATION APPARATUS AND METHOD OF USING SAME FOR ABLATION OF AN ARBITRARY VOLUME

(71) Applicant: NORTHWESTERN UNIVERSITY, Evanston, IL (US)

(72) Inventors: Alan V. Sahakian, Northbrook, IL (US); Yearnchee C. Wang, Mill Creek, WA (US)

(73) Assignee: Northwestern University, Evanston, IL (US)

( * ) Notice: Subject to any disclaimer, the term of this patent is extended or adjusted under 35 U.S.C. 154(b) by 705 days.

(21) Appl. No.: 14/918,703

(22) Filed: Oct. 21, 2015

(65) Prior Publication Data
US 2016/0113707 A1    Apr. 28, 2016

Related U.S. Application Data (60) Provisional application No. 62/068,703, filed on Oct. 26, 2014, provisional application No. 62/068,210, filed on Oct. 24, 2014.

(51) Int. Cl.
*A61B 18/14* (2006.01)
*A61N 1/32* (2006.01)
(Continued)

(52) U.S. Cl.
CPC .. *A61B 18/1477* (2013.01); *A61B 2018/0016* (2013.01); *A61B 2018/00196* (2013.01);
(Continued)

(58) Field of Classification Search
CPC .............. A61B 2018/00613; A61N 1/327
See application file for complete search history.

(56) References Cited

U.S. PATENT DOCUMENTS 6,009,347 A * 12/1999 Hofmann ............... A61N 1/325
604/20
6,104,960 A * 8/2000 Duysens ............... A61N 1/0551
607/117
(Continued)

FOREIGN PATENT DOCUMENTS

WO    2005065284    7/2005

OTHER PUBLICATIONS

Gilbert, Richard A., Mark J. Jaroszeski, and Richard Heller, "Novel electrode designs for electrochemotherapy," Biochimica et Biophysica Acta (BBA)—General Subjects 1334, 9-14, Jan. 1997.
(Continued)

*Primary Examiner* — Ronald Hupczey, Jr.
(74) *Attorney, Agent, or Firm* — Banner & Witcoff, Ltd.

(57) ABSTRACT

An electroporation apparatus and the method of using same are provided. The apparatus allows for the ablation of an area of tissue of arbitrary volume. The apparatus includes a plurality of conductive electrodes attached to a base plate and electrically connected to a pulse generator to allow individual electrical actuation of the electrodes. In use, the electrodes are inserted into an area of tissue to be ablated, such that the electrodes are in a first position. Predetermined ones of the electrodes are then activated to ablate tissue surrounding the activated electrodes, while leaving other ones of the electrodes un-activated. The electrodes are then moved to a second position which is different than the first position, and predetermined ones of the electrodes are then activated to ablate tissue surrounding the activated electrodes, while leaving other ones of the electrodes un-activated.

20 Claims, 10 Drawing Sheets

(51) Int. Cl.
  *A61B 18/00* (2006.01)
  *A61B 18/12* (2006.01)
  *A61N 1/05* (2006.01)
(52) U.S. Cl.
  CPC .............. *A61B 2018/00613* (2013.01); *A61B 2018/124* (2013.01); *A61B 2018/143* (2013.01); *A61B 2018/1427* (2013.01); *A61B 2018/1467* (2013.01); *A61B 2018/1475* (2013.01); *A61N 1/0502* (2013.01); *A61N 1/327* (2013.01)

(56) References Cited

U.S. PATENT DOCUMENTS

| | | | |
|---|---|---|---|
| 6,208,893 | B1 | 3/2001 | Hofmann et al. |
| 6,520,927 | B1* | 2/2003 | Unsworth .............. A61B 18/24 |
| | | | 128/898 |
| 8,231,603 | B2 | 7/2012 | Hobbs et al. |
| 8,282,631 | B2 | 10/2012 | Davalos et al. |
| 2004/0220444 | A1* | 11/2004 | Hogendijk ............ A61M 25/01 |
| | | | 600/7 |
| 2009/0254019 | A1* | 10/2009 | Gehl .................. A61B 18/1477 |
| | | | 604/21 |
| 2011/0118732 | A1 | 5/2011 | Rubinsky et al. |
| 2012/0277741 | A1 | 11/2012 | Davalos et al. |
| 2012/0310230 | A1* | 12/2012 | Willis .................... A61N 1/327 |
| | | | 606/33 |
| 2013/0281968 | A1 | 10/2013 | Davalos et al. |

OTHER PUBLICATIONS

Davalos, Rafael V., L. M. Mir, and B. Rubinsky, "Tissue ablation with irreversible electroporation," Ann. Biomed. Eng. 33, 223-231, Feb. 2005.

Neal II, R. E., Singh, R., Hatcher, H. C., Kock, N. D., Torti, S. V., and Davalos, R. V., "Treatment of breast cancer through the application of irreversible electroporation using a novel minimally invasive single needle electrode," Breast Cancer Research and Treatment 123, 295-301, Jan. 2010.

Rubinsky, Boris., "Irreversible Electroporation in Medicine," Technology in Cancer Research and Treatment 6, 255, Aug. 2007.

* cited by examiner

ELECTROPORATION APPARATUS AND METHOD OF USING SAME FOR ABLATION OF AN ARBITRARY VOLUME

This application claims the domestic priority of U.S. provisional application Ser. No. 62/068,210 filed on Oct. 24, 2014, and claims the domestic priority of U.S. provisional application Ser. No. 62/068,703 filed on Oct. 26, 2014, the disclosures of which are herein incorporated by reference in their entireties.

FIELD OF THE DISCLOSURE

The present invention relates to an electroporation apparatus and method of using same which is used for ablation of tissue having an arbitrary volume. The electroporation apparatus is useful in treating diseases without damaging healthy tissues, and may be used to treat cancer (carcinoma) treatment and non-malignant cyst or abscess/growth treatment.

BACKGROUND OF THE DISCLOSURE

Electroporation of cells occurs when the cells are exposed to an electric field of sufficient strength, even very briefly. Electroporation can be reversible in a particular range of electric field strength, or irreversible at higher electrical field strengths.

In the case of reversible electroporation, pores form in cell membranes, increasing their permeability, and then close over time. Reversible electroporation can be used to introduce agents into cells, including chemotherapeutic agents. Irreversible electroporation is a tissue ablation modality that utilizes high-strength electric fields to cause apoptosis and necrosis of tissues and cells. It is preferential to thermal ablation due to its sharp ablation margin, apoptosis effects, and preservation of important physiological structures such as blood vessels.

Both reversible and irreversible ablation have been used in the treatment of tumors, typically with pairs or small arrays of electrodes. In current practice, the electrodes are inserted into the tissue to be ablated and then electrical pulses are applied, after which the electrodes are removed. Current electrode designs in tumor ablation (with reversible or irreversible electroporation) are not designed to ablate a tumor of arbitrary volume. These electrode designs have fixed ablation profiles, either cylindrical, spherical, or elliptical.

SUMMARY

An electroporation apparatus and the method of using same in accordance with some example embodiments includes a pulse generator, a base plate and a plurality of conductive electrodes attached to the base plate and electrically connected to the pulse generator to allow individual electrical actuation of the electrodes. The electroporation apparatus allows for the ablation of an area of tissue of any arbitrary volume, which may be an arbitrary three-dimensional volume, with the use of reversible or irreversible electroporation, creating an ablation profile that matches the desired volume to be destroyed with sharp margins. In an embodiment, the electroporation apparatus may further include support plate which is moveably connected to the base plate. The plurality of conductive electrodes may be provided in an array and attached to the base plate, and extend through the support plate. Each electrode is electrically connected to the pulse generator to allow individual electrical actuation of the electrodes by the pulse generator. Each electrode may have an insulating material provided on at least one portion thereof. Each electrode may have a sharpened tip to provide for penetration of the electrode through the tissue. Predetermined ones of the electrodes may have a path therethrough to allow infusion of an agent into the tissue.

In use, the plurality of conductive electrodes are inserted into an area of tissue to be ablated, such that the electrodes are in a first position. Thereafter, predetermined ones of the electrodes are activated to ablate tissue surrounding the activated electrodes when the electrodes are in the first position, while leaving other ones of the electrodes un-activated. Next, the electrodes are moved to a second position which is different than the first position and predetermined ones of the electrodes are activated to ablate tissue surrounding the activated electrodes, while leaving other ones of the electrodes un-activated. In some instances, the electrodes are moved to a third position which is different than the first or second positions and all of the electrodes are activated to ablate tissue surrounding the activated electrodes.

This Summary is provided merely for purposes of summarizing some example embodiments so as to provide a basic understanding of some aspects of the disclosure. Accordingly, it will be appreciated that the above described example embodiments are merely examples and should not be construed to narrow the scope or spirit of the disclosure in any way. Other embodiments, aspects, and advantages of various disclosed embodiments will become apparent from the following detailed description taken in conjunction with the accompanying drawings which illustrate, by way of example, the principles of the described embodiments.

BRIEF DESCRIPTION OF THE DRAWINGS

The organization and manner of the structure and operation of the disclosed embodiments, together with further objects and advantages thereof, may best be understood by reference to the following description, taken in connection with the accompanying drawings, which are not necessarily drawn to scale, wherein like reference numerals identify like elements in which.

DETAILED DESCRIPTION OF THE ILLUSTRATED EMBODIMENTS

While the invention may be susceptible to embodiment in different forms, there is shown in the drawings, and herein will be described in detail, specific embodiments with the understanding that the present disclosure is to be considered an exemplification of the principles of the invention, and is not intended to limit the invention to that as illustrated and described herein. Therefore, unless otherwise noted, features disclosed herein may be combined together to form additional combinations that were not otherwise shown for purposes of brevity.

An electroporation apparatus 20 and method of using same is provided for the therapeutic application of electroporation. The electroporation apparatus 20 allows for the ablation of an area 80 of tissue of any arbitrary volume, which may be an arbitrary three-dimensional volume, with the use of reversible or irreversible electroporation, creating an ablation profile that matches the desired volume to be destroyed with sharp margins. The electroporation apparatus 20 includes a plurality of individual electrodes 24 which may be formed as an array 22. The method includes infusion of an agent and electroporation of the agent into an area 80 of tissue to be ablated. The agent may be a chemotherapeutic agent, medication, contrast die, saline for example. The agent is injected into the tissue, and at least one voltage pulse is applied between electrodes 24 disposed in the tissue, thereby generating electric fields in the cells of the tissue. The electrodes 24 enable the in vivo positioning of the electrodes 24 in or adjacent to subsurface tumors or other tissue. Such therapeutic treatment is called electroporation therapy (EPT), a form of electrochemotherapy. The electrical pulse can be delivered before, at the same time as, or after, the application of the agent. The chemical composition of the agent will dictate the most appropriate time to administer the agent in relation to the administration of the electric pulse. Electroporation can help minimize the amount of a chemotherapeutic agent used. The electroporation apparatus 20 allows surgical oncologists and interventional radiologists to control the destruction of tissue during treatment.

Figures 1, 1A:
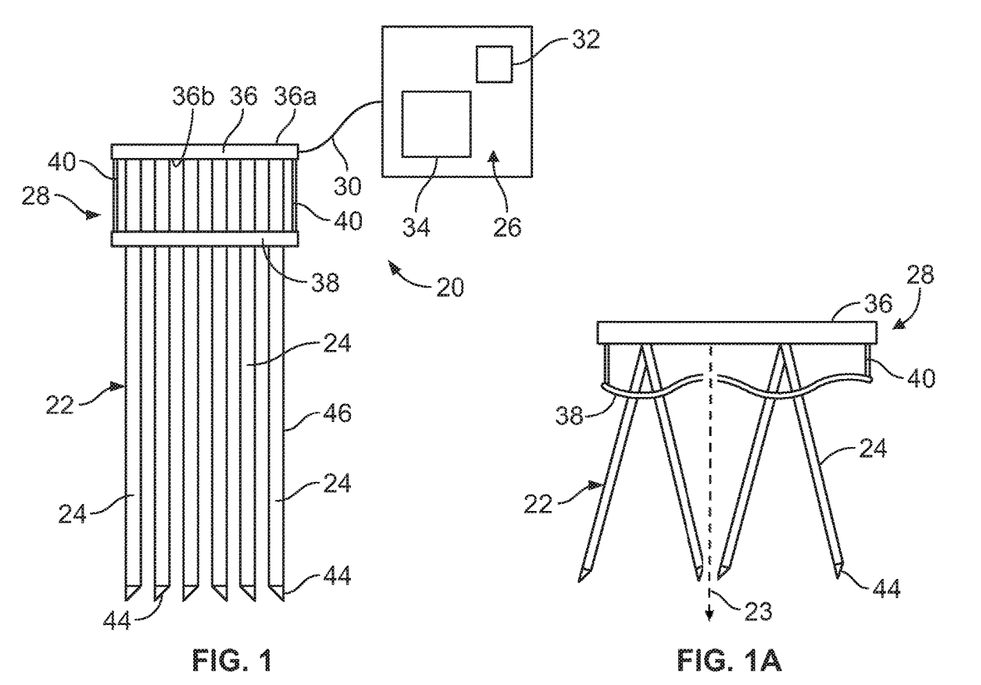
FIG. 1 is a side elevation view of an electroporation apparatus which includes a plurality of electrodes and a pulse generator.
FIG. 1A is a side elevation view of an alternate electrode apparatus.

Referring to FIG. 1, an embodiment of the electroporation apparatus 20 is illustrated. The electroporation apparatus 20 includes an electrode apparatus 28 which includes the plurality of individual electrodes 24, and a pulse generator 26 for generating high voltage pulses. The pulse generator 26 is connected to the electrode apparatus 22 by a cable 30. The pulse generator 26 includes a processor 32 having software therein which controls the pulses generated by the pulse generator 26 as described herein, and a control panel 34 for operating the pulse generator 26. The control panel 34 may have various indicators to indicate to the operator various conditions and parameters. A precise and controlled voltage must be applied to tissue to be ablated in order to provide the optimum portion of the cells of the tissue. The electroporation apparatus 20 provides for applying pulses to selected electrodes 24 as the electrodes 24 are inserted into, or refracted from, the tissue being ablated.

The electrode apparatus 28 is formed of the plurality of electrodes 24, a base plate 36 from which the electrodes 24 extend, a support plate 38 through which the electrodes 24 pass through, and a structure 40 which connects the plates 36, 38 together while allowing the plates 36, 38 to move relative to each other.

Figures 3, 3A, 4, 5, 6:
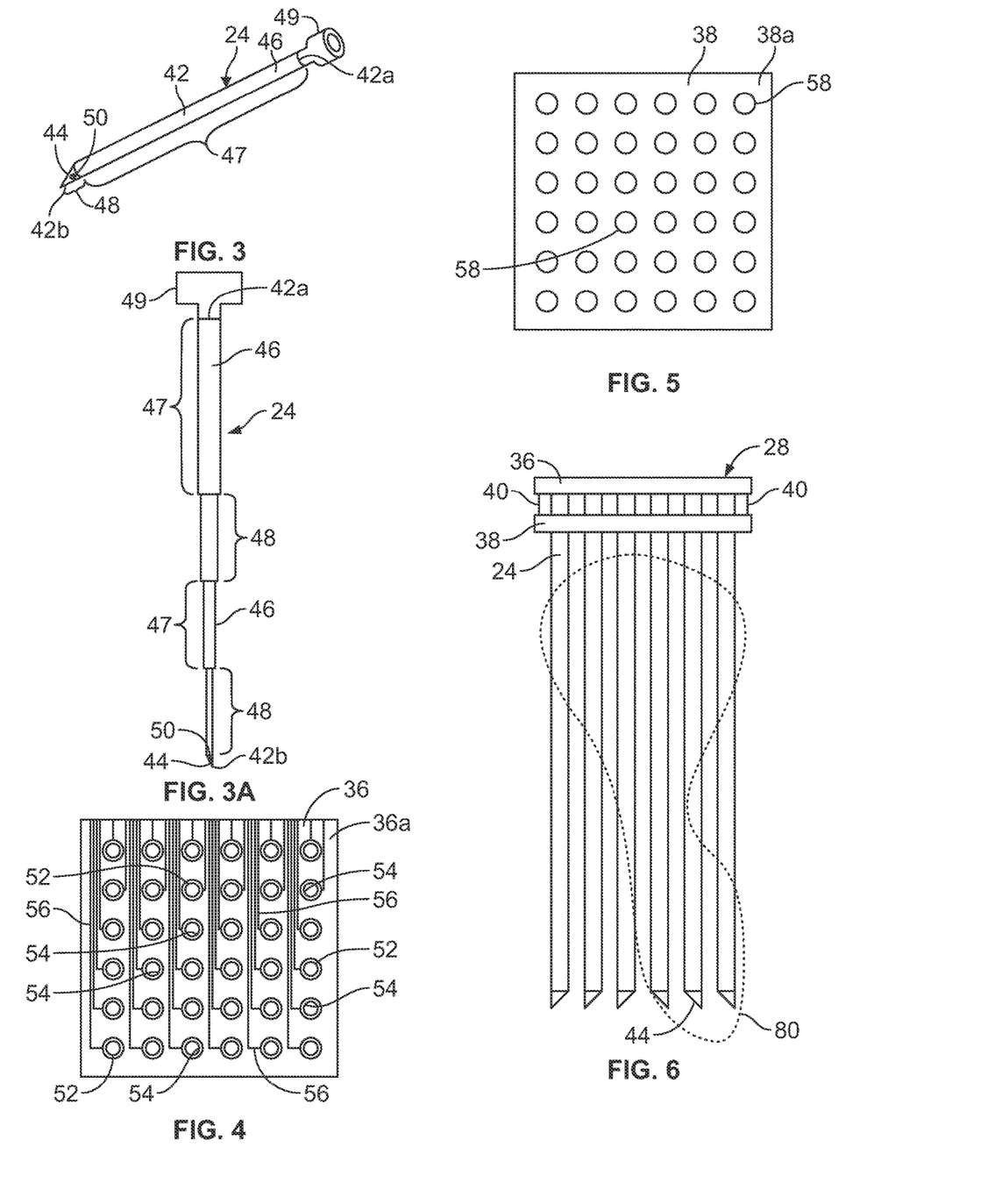
FIG. 3 is a perspective view of a first embodiment of an electrode used in the electroporation apparatus.
FIG. 3A is a perspective view of a second embodiment of an electrode used in the electroporation apparatus.
FIG. 4 is a plan view of a base plate with electrodes shown in cross-section, which form part of the electroporation apparatus.
FIG. 5 is a plan view of a support plate which forms part of the electroporation apparatus.
FIG. 6 is a side elevation view of a portion of the electroporation apparatus shown in a fully inserted position into the tissue around and through the tissue to be ablated.

As shown in FIGS. 3 and 3A, the electrodes 24 are formed from an elongated member 42 having a proximal end 42a and a distal end 42b, which defines a length therebetween and along which a centerline is defined. The distal end 42b of the needle forms a tip 44. The tip 44 may be formed from a sharp point or a drill in order to allow the electrodes 24 to penetrate the tissue to be ablated. The electrodes 24 are constructed of any suitable electrically conductive materials, such as for example but not limited to stainless steel, platinum, iridium, gold. In an embodiment as shown in FIG. 3, the electrode 24 has an insulating material 46 which extends along a portion 47 of the length of the electrode 24, and an uninsulated portion 48 where the electrical pulses will be transmitted. The uninsulated portion 48 may be at the tip 44, however, the uninsulated portion 48 may be formed anywhere along the length of the electrode 24. In an embodiment as shown in FIG. 3A, the electrode 24 has an insulating material 46 which extends along portions 47 of the length of the electrode 24, and uninsulated portions 48 where the electrical pulses will be transmitted. As shown in FIG. 3A, the insulating material 46 alternates with the uninsulated portions 48. The insulating material 46 is of any suitable material, such as for example but not limited to conformal paint or lacquer, with the tip 44 being immersed into a solvent to remove the conformal paint or lacquer from the tip 44, or a rubber coating. In certain applications, the tissue to be treated lies beneath healthy tissue, and the insulating material 46 isolates the overlying tissue from the pulses. The electrodes 24 may also take any suitable form and have any suitable length for the particular application. The electrodes 24 may be of the same length, or may have differing lengths. The electrodes 24 are small, for example but not limited to 0.05 mm, and have a small gauge, for example but not limited to 22 gauge or higher. One or more of the electrodes 24 may be hollow and have a suitable connector 49 at the proximal end 42a. The distal end 42b of each hollow electrode 24 has an outlet, such as an open end or one or more ports 50. This provides a path through the electrode 24 to enable the infusion of drugs or genes through the electrode 24 and into the tissue to be ablated. While two examples of electrodes 24 are shown in FIGS. 3 and 3A, it is to be understood that other forms of electrodes can be used, for example, a thin cylinder, a thin rectangular prism, etc.

As best shown in FIGS. 1 and 4, the base plate 36 has a proximal face 36a and a distal face 36b and is formed of an insulative material. A plurality of through holes 52 arranged in an array 22 are provided through the base plate 36. The respective proximal ends 42a of the electrodes 24 are attached with the through holes 53 and the electrodes 24 extend from the distal face 36b of the base plate 36. The through holes 52 are arranged in an array. Preferably, the array has a plurality of rows and columns of through holes 52, but the array may have a single row of through holes 52.

Figure 1B:
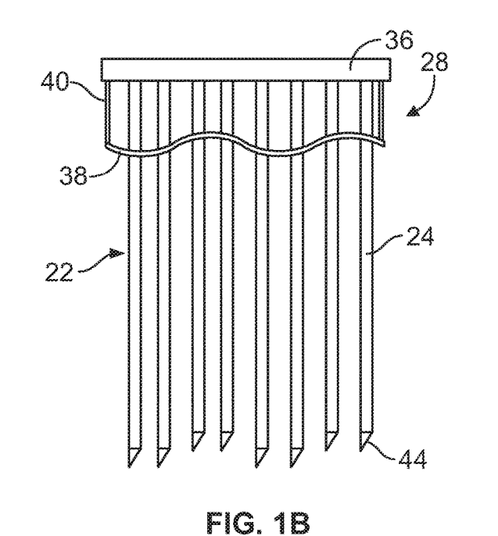
FIG. 1B is a side elevation view of another alternate electrode apparatus.
Figure 2:
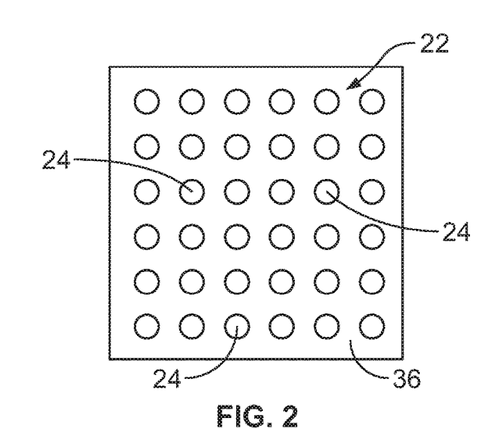
FIG. 2 is a cross-sectional view through lines 2-2 of FIG. 1.

As an example as shown in FIG. 4, the array is six-by-six, wherein six columns and six rows of through holes 52 are provided. The through holes 52 are preferably equally spaced from each other, with the rows being parallel to each other, and the columns being parallel to each other. It is to be understood, however, that a variety of shapes of arrays can be provided. The base plate 36 may be take a variety of shapes, such as planar as shown in FIGS. 1, 1A and 1B, curved such as wavy or in an arc, etc.

Each through hole 52 has a conductive surface 54 to which the respective electrode 24 is attached. Conductors 56 are provided on the proximal face 36a or on the distal face 36b or extend through the base plate 36, and the conductors 56 extend from the respective conductive surface 54 of each through hole 52, thereby forming a path, and connects the respective conductive surface 54 to the pulse generator 26. The pulse generator 26 is attached to the paths via cable 30. The respective paths are electrically isolated from each other by the insulative material of which the base plate 36 is formed. The conductors 56 can be electrically independent, allowing for different voltages or polarities. As such, each electrode 24 is electrically connected to the pulse generator 26 by the path formed by the conductive surface 54 in the through hole 52 and the conductor 56 on the base plate 36 to enable each electrode 24 to be selectively activated by the pulse generator 26. The base plate 36 may be formed of a plurality of layers with the conductors 56 being formed on the differing layers.

As shown in FIG. 5, the support plate 38 is formed of an insulative material, and has a proximal face 38a and a distal face 38b. A plurality of through holes 58 are provided through the support plate 38. The proximal face 38a of the support plate 38 is proximate to the distal face 36b of the base plate 36. In an embodiment as shown in FIGS. 1 and 1B, the through holes 58 in the support plate 38 are provided in the same array as the array that is provided in the base plate 36, such that the through holes 58 in the support plate 38 linearly align with the through holes 52 in the base plate 36 and the centerline of the electrodes 24 are parallel to each other. In an embodiment as shown in FIG. 1A, the through holes 58 in the support plate 38 are provided in a different array to that of the array provided in the base plate 36, such that the through holes 58 in the support plate 38 do not align with the through holes 52 in the base plate 36. In FIG. 1A, this allows the centerlines of the electrodes 24 to be at an angle relative to the base plate 36 instead of being orthogonal to the base plate 36 as shown in FIGS. 1 and 1B. As shown in FIG. 1B, the electrodes 24 may extend distally toward an imaginary longitudinal axis 23 that is perpendicular to the base plate 36 and/or support plate 38. In each embodiment, the electrodes 24 extend through the through holes 58 in the support plate 38 and are attached thereto by a friction fit. The support plate 38 may be take a variety of shapes, such as planar as shown in FIG. 1, curved such as wavy as shown in FIGS. 1A and 1B, or in an arc, etc.

The base plate 36 and the support plate 38 are connected together by structure 40 which spaces the plates 36, 38 apart from each other, while allowing for the relative movement of the base plate 36 relative to the support plate 38. The actuation of the structure 40 is preferably controlled by the processor 32, but may also be hand-actuated. Such structures 40 may include, but are not limited to, telescoping legs, a driven ball screw drive, pistons.

In use, the area 80 where the tissue to be ablated is imaged by medical imagery techniques which techniques are known in the art. Based upon the information obtained from the medical imaging, the volume and shape of the tissue to be ablated is determined using computation models.

Figure 7A:
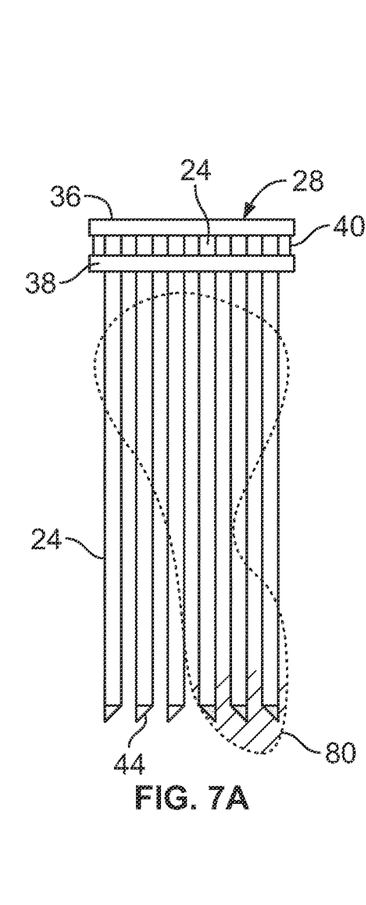
FIG. 7A-7H are side elevation views of a portion of the electroporation apparatus showing the steps of the electrodes being withdrawn from the tissue around and through the tissue to be ablated.
Figure 7B:
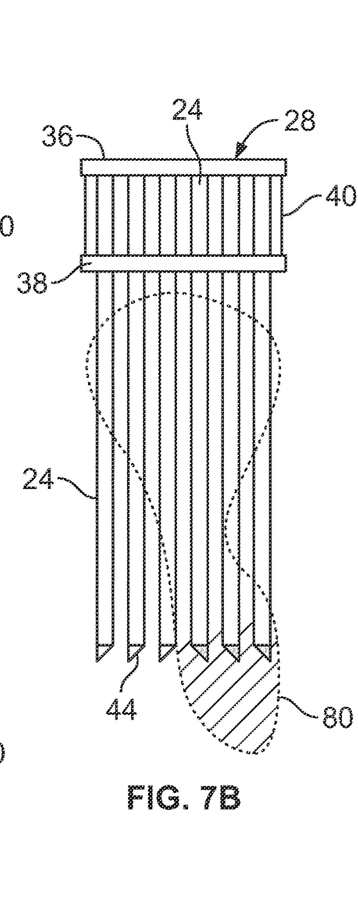
Figure 7C:
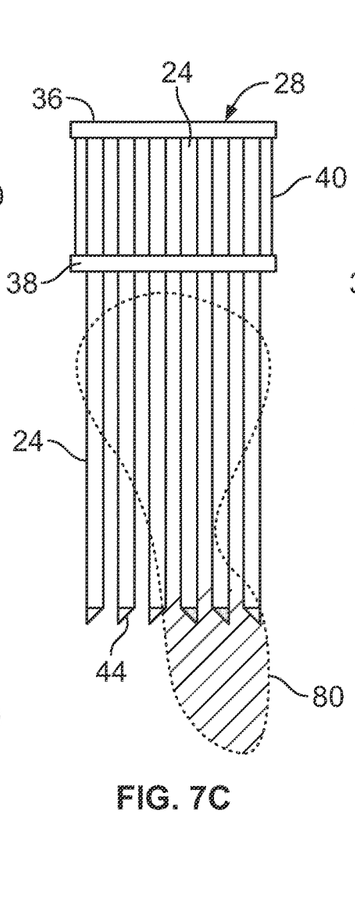
Figure 7D:
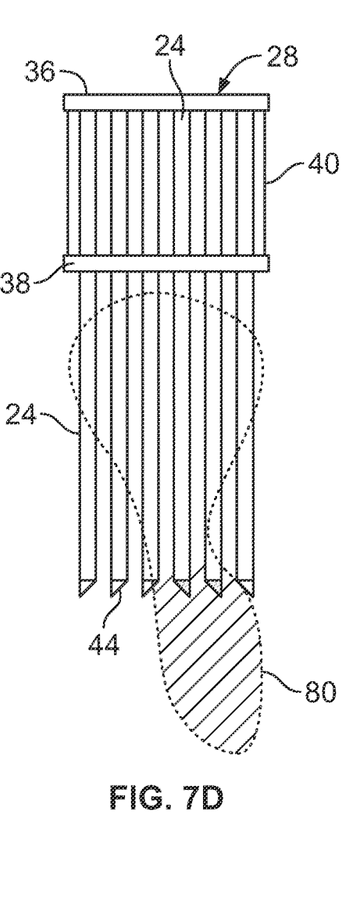
Figure 7E:
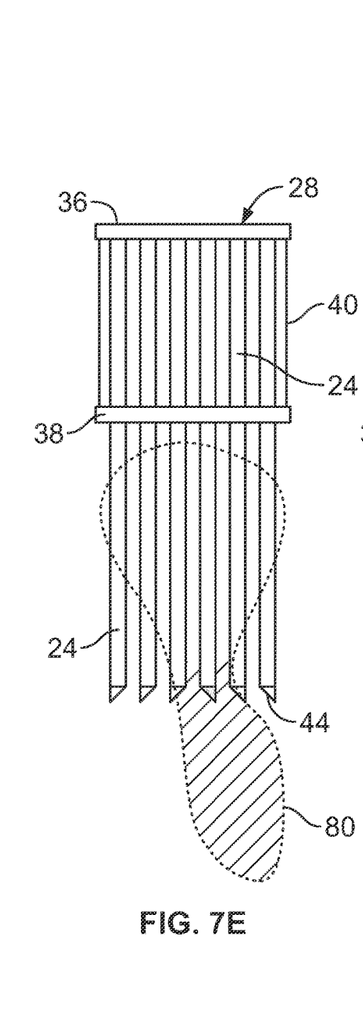
Figure 7F:
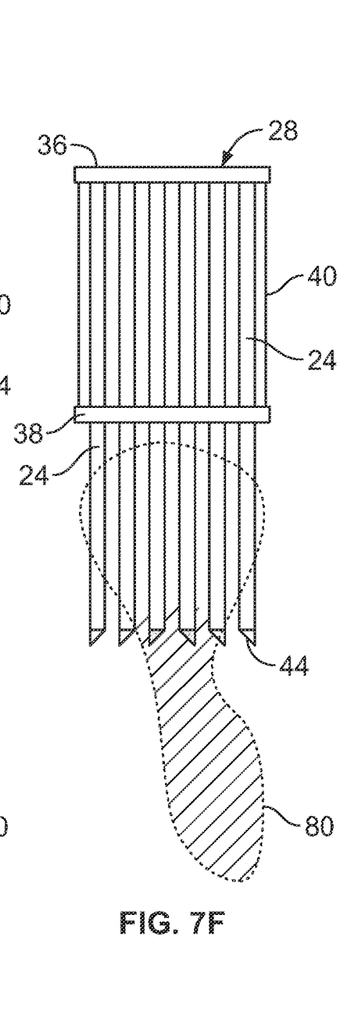
Figure 7G:
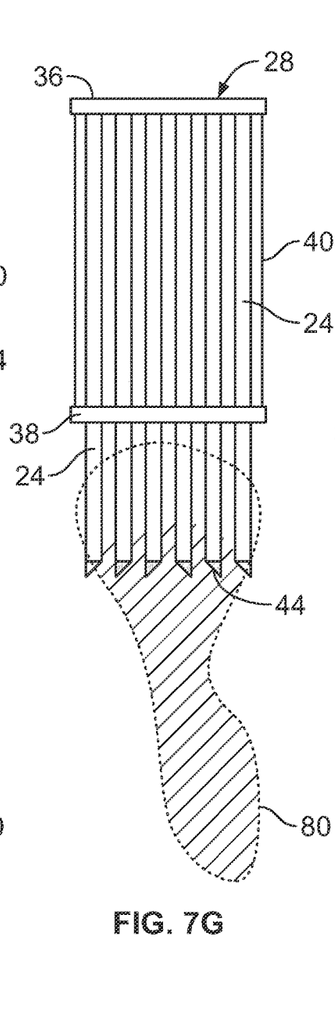
Figure 7H:
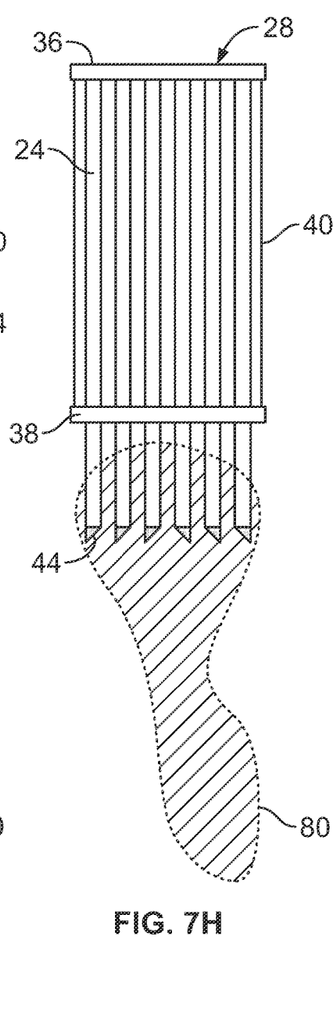
Figure 8A:
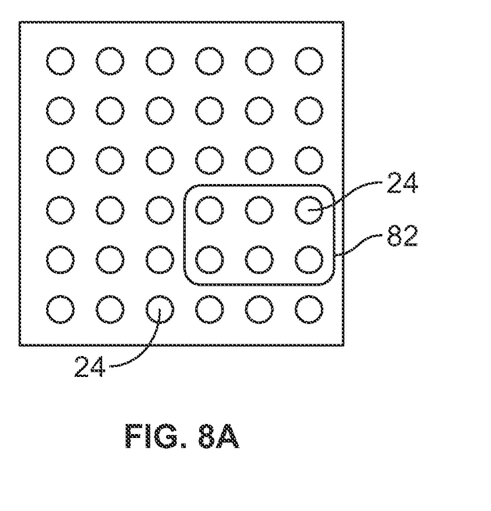
FIG. 8A-8H are plan elevation views of the electrodes showing which electrodes are activated during the steps shown in FIGS. 7A-7H.
Figure 8B:
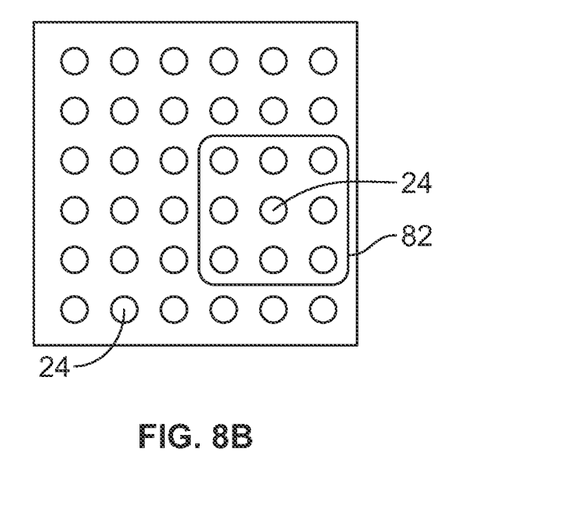
Figure 8C:
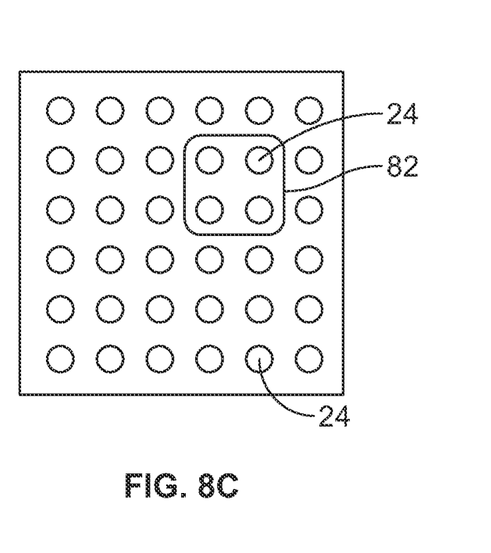
Figure 8D:
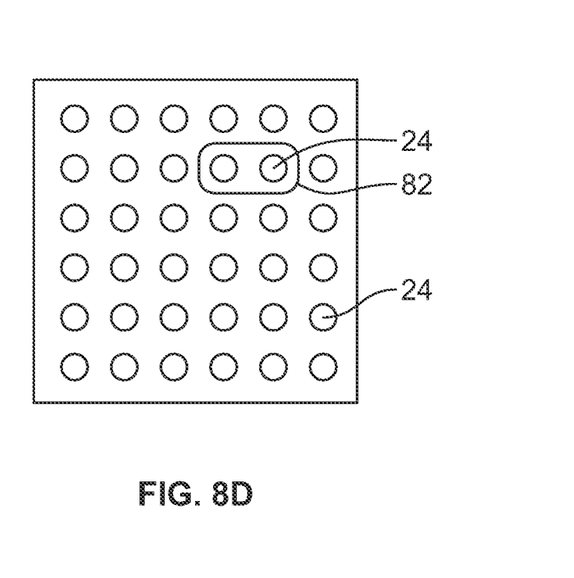
Figure 8E:
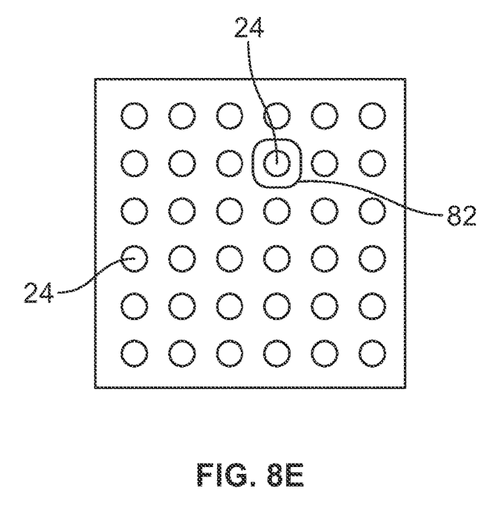
Figure 8F:
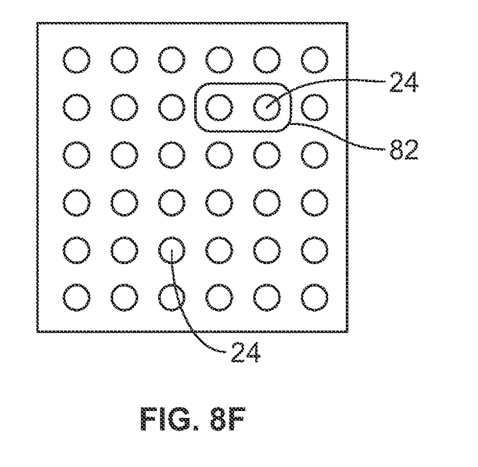
Figure 8G:
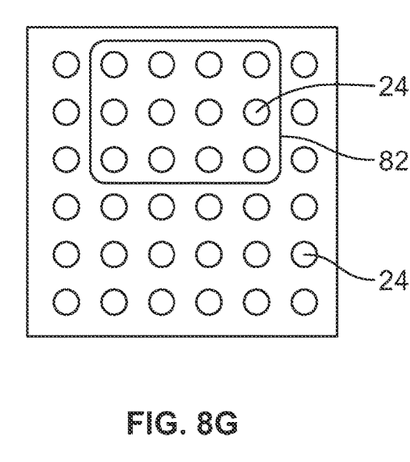
Figure 8H:
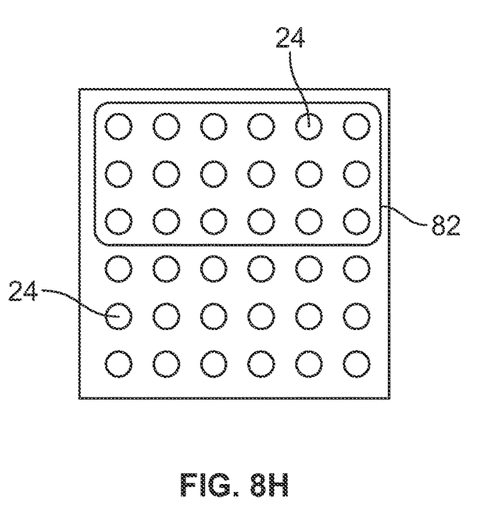

In a first embodiment, the support plate 38 is positioned against, and held firmly against, the accessible surface of the tissue to be ablated. Thereafter, the electrodes 24 are fully inserted into the tissue around and through the tissue to be ablated, and then certain ones of the electrodes 24 are activated in a predetermined sequence while the electrodes 24 are being withdrawn from the tissue to create a specific three dimensional pattern of ablation conforming to the tumor and sparing the surrounding tissue. The tips 44 penetrate the tissue to insert the electrodes 24 into the tissue around and through the tissue to be ablated. Once fully inserted, the electrodes 24 are positioned in a first position as shown in FIG. 6, wherein the uninsulated portions 48 of the electrodes 24 are positioned at the furthest point away from the plates 36, 38 which corresponds to the distal end of the area 80 of tissue to be ablated. At this position, the electrodes 24 which are within the tissue to be ablated are selectively activated by the pulse generator 26 to apply a voltage pulse to ablate the surrounding tissue as shown in FIGS. 7A and 8A, while any electrodes 24 that are not within the tissue to be ablated are not activated. If desired, agent can be supplied to the tissue through the electrodes 24. Thereafter, the electrodes 24 are retracted to a second position, and, as shown in FIGS. 7B and 8B, the electrodes 24 which are within the tissue to be ablated are selectively activated by the pulse generator 26 to apply a voltage pulse to ablate the surrounding tissue, while any electrodes 24 that are not within the tissue to be ablated are not activated. If desired, agent can be supplied to the tissue through the electrodes 24. Next, the electrodes 24 are retracted to a third position, and, as shown in FIGS. 7C and 8C, the electrodes 24 which are within the tissue to be ablated are selectively activated by the pulse generator 26 to apply a voltage pulse to ablate the surrounding tissue, while any electrodes that are not within the tissue to be ablated are not activated. If desired, agent can be supplied to the tissue through the electrodes 24. This sequence of activation/delivery of agent, retraction, activation/delivery of agent, retraction, etc. is repeated as many times as necessary to completely ablate the tissue. The sequence of voltage pulsing may have varying parameters, which creates three-dimensional regions of electroporation with desired shapes and sizes. The electrodes 24 are driven with electrical pulses sufficient to reach tissue the desired electroporation threshold. As shown in FIGS. 7A-7H and 8A-8H for the exemplary tissue being ablated, activation occurs at eight different times and locations along the tissue, with different electrodes 24 being activated as the electrodes 24 are positioned within the tissue. In each instance of activation of the selected electrodes 24, the activation is controlled by the processor 32. Preferably, the processor 32 uses information from the medical imagery to ensure the proper placement of the electrodes 24 and the activation of the correct electrodes 24 to allow for real-time monitoring of ablation volume and electrode placement. At least two electrodes 24 must be activated into order to pass the electrical pulse between the electrodes 24 and ablate the surrounding tissue. The retraction of the electrodes 24 may be performed using the structure 40, or may be performed by hand refraction. Before the procedure is performed, the processor 32 employs software to optimize the retraction sequence using a computational model. In FIGS. 7A-7H, the activated electrodes 24 are shown with a darkened tip 44, while the un-activated electrodes 24 are shown with an undarkened tip 44. In FIGS. 8A-8H, the activated electrodes 24 are shown circled and labeled with the reference number 82, with the remainder being un-activated.

Figure 9A:
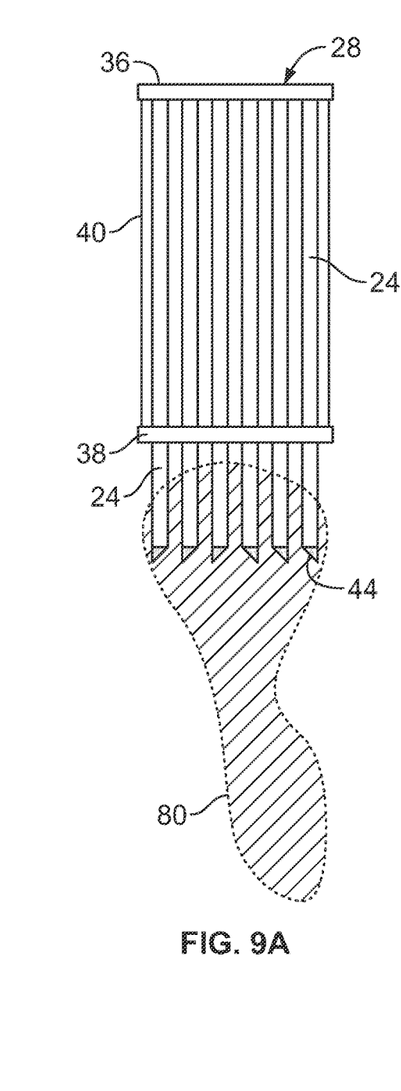
FIG. 9A-9H are side elevation views of a portion of the electroporation apparatus showing the steps of the electrodes being withdrawn from the tissue around and through the tissue to be ablated.
Figure 9B:
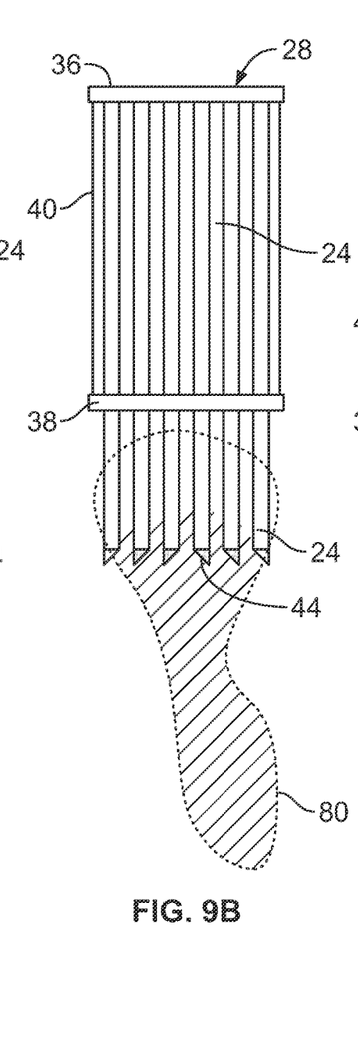
Figure 9C:
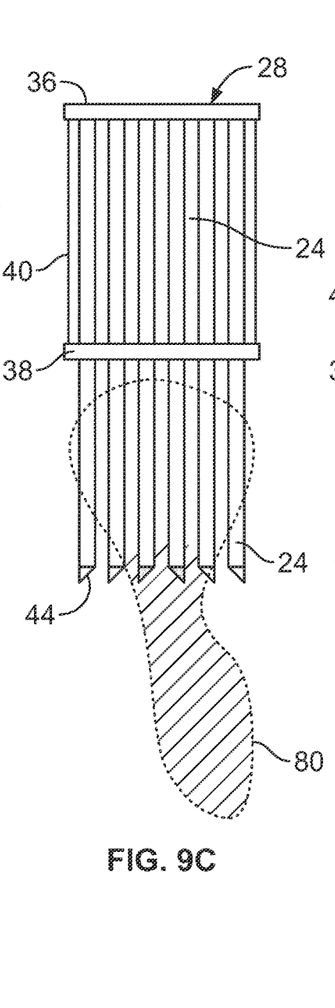
Figure 9D:
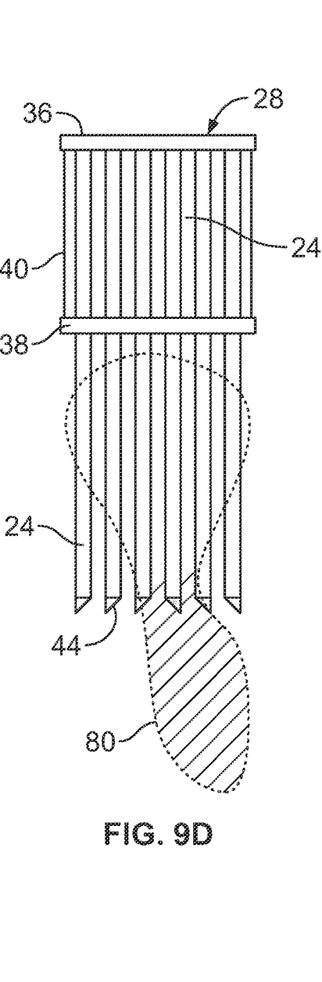
Figure 9E:
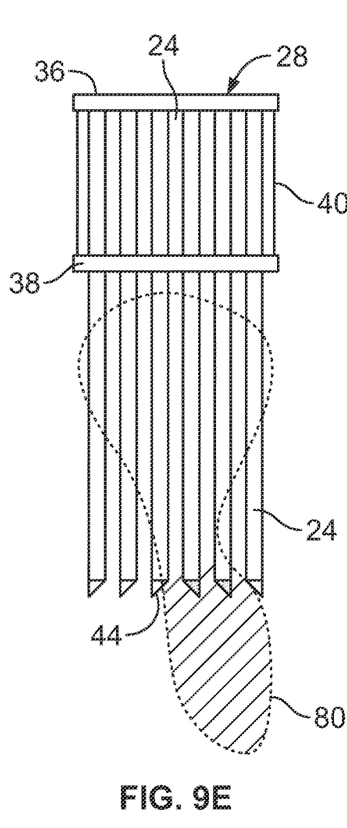
Figure 9F:
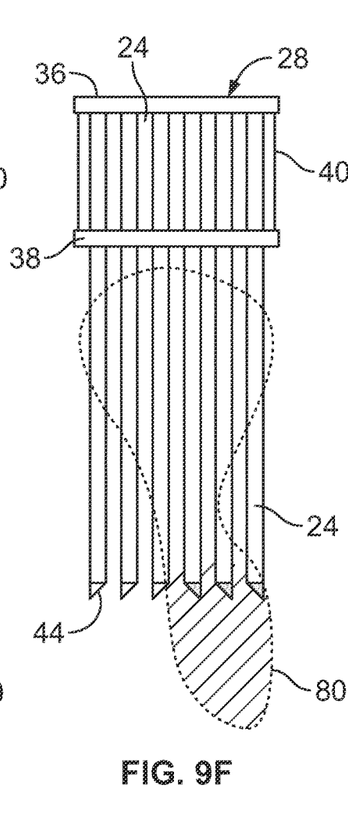
Figure 9G:
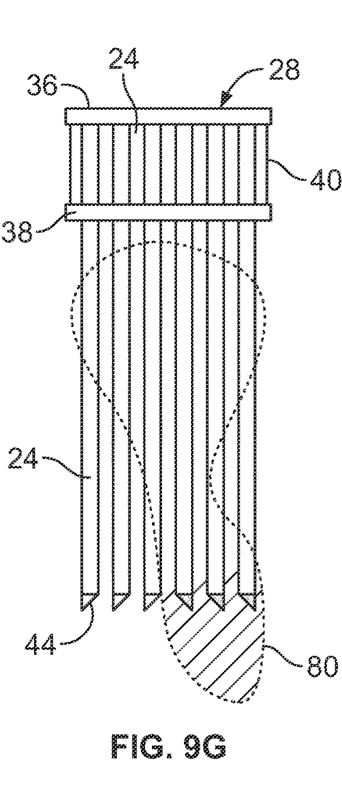
Figure 9H:
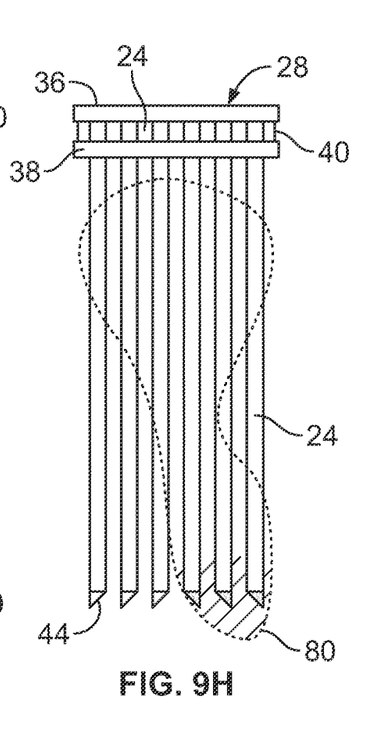
Figure 10A:
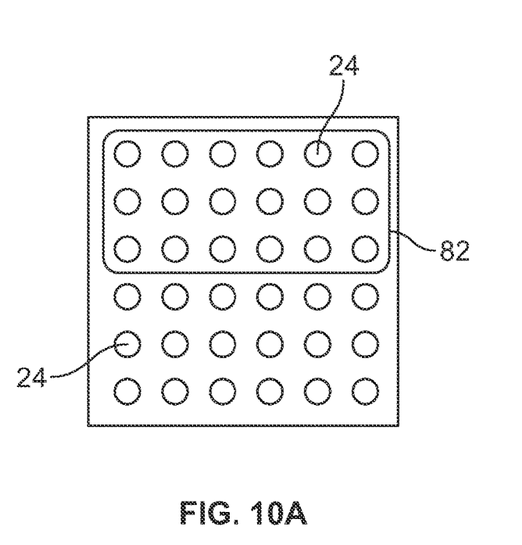
FIG. 10A-10H are plan elevation views of the electrodes showing which electrodes are activated during the steps shown in FIGS. 7A-7H.
Figure 10B:
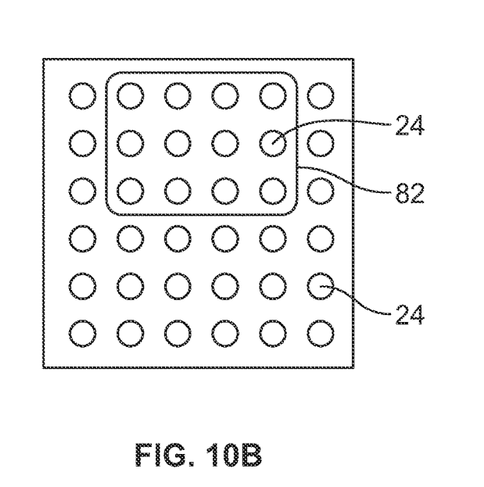
Figure 10C:
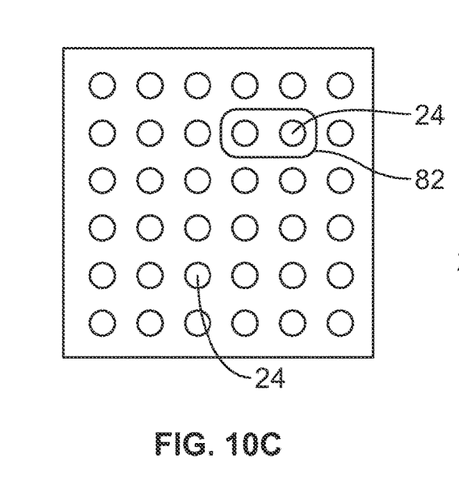
Figure 10D:
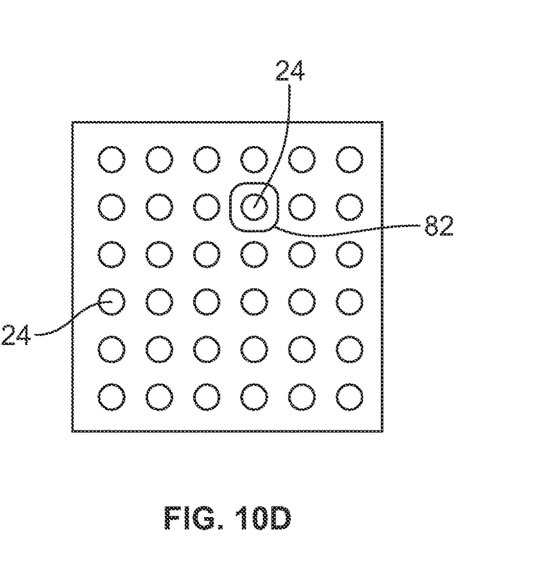
Figure 10E:
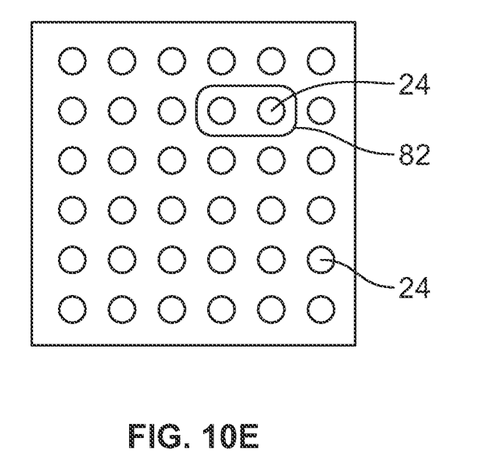
Figure 10F:
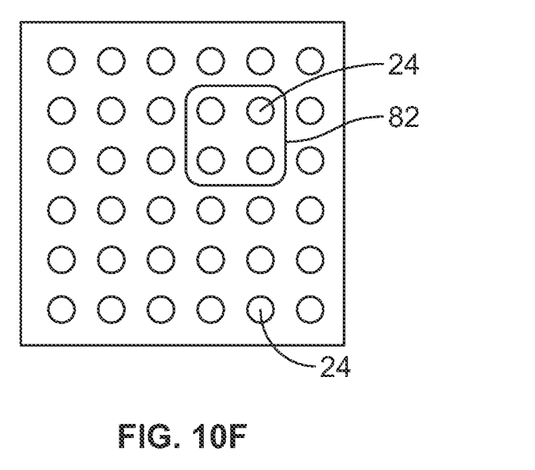
Figure 10G:
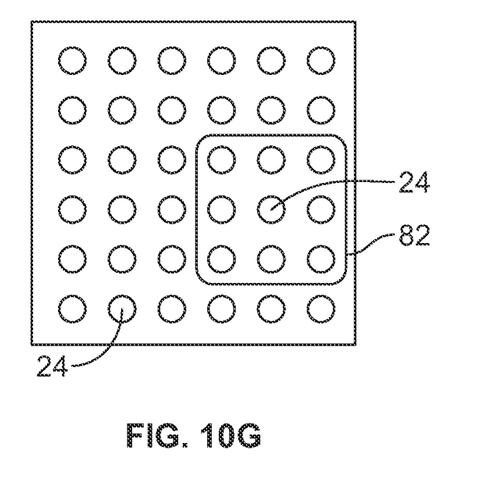
Figure 10H:
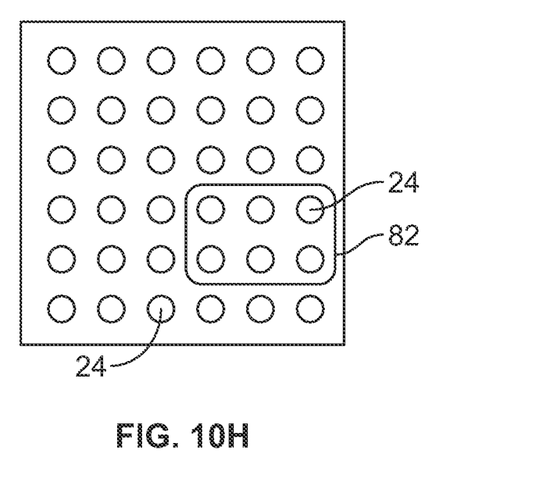

In a second embodiment, the support plate 38 is positioned against, and held firmly against, the accessible surface of the tissue to be ablated. Thereafter, the electrodes 24 are partially inserted into the tissue around and through the tissue to be ablated and then are certain ones of the electrodes 24 are activated in a predetermined sequence while the electrodes 24 are being inserted into the tissue to create a specific three dimensional pattern of ablation conforming to the tumor and sparing the surrounding tissue. The tips 44 penetrate the tissue to insert the electrodes 24 into the tissue around and through the tissue to be ablated. Once partially inserted, the electrodes 24 are positioned in a first position as shown in FIGS. 9A and 10A, and the electrodes 24 which are within the tissue to be ablated are selectively activated by the pulse generator 26 to apply a voltage pulse to ablate the surrounding tissue, while any electrodes 24 that are not within the tissue to be ablated are not activated. If desired, agent can be supplied to the tissue through the electrodes 24. Thereafter, the electrodes 24 are inserted into the tissue to a second position, and, as shown in FIGS. 9B and 10B, the electrodes 24 which are within the tissue to be ablated are selectively activated by the pulse generator 26 to apply a voltage pulse to ablate the surrounding tissue, while any electrodes 24 that are not within the tissue to be ablated are not activated. If desired, agent can be supplied to the tissue through the electrodes 24. Next, the electrodes 24 are inserted into the tissue to a third position, and, as shown in FIGS. 9C and 10C, the electrodes 24 which are within the tissue to be ablated are selectively activated by the pulse generator 26 to apply a voltage pulse to ablate the surrounding tissue, while any electrodes 24 that are not within the tissue to be ablated are not activated. If desired, agent can be supplied to the tissue through the electrodes 24. This sequence of activation/delivery of agent, insertion, activation/delivery of agent, insertion, etc. is repeated as many times as necessary to completely ablate the tissue. The sequence of voltage pulsing may have varying parameters, which creates three-dimensional regions of electroporation with desired shapes and sizes. The electrodes 24 are driven with electrical pulses sufficient to reach tissue the electroporation threshold. As shown in FIGS. 9A-9H and 10A-10H for the exemplary tissue being ablated, activation occurs at eight different times and locations along the tissue, with different electrodes 24 being activated as the electrodes 24 are positioned within the tissue. In each instance of activation of the selected electrodes 24, the activation is controlled by the processor 32. Preferably, the processor 32 uses information from the medical imagery to ensure the proper placement of the electrodes 24 and the activation of the correct electrodes 24 to allow for real-time monitoring of ablation volume and electrode placement. At least two electrodes 24 must be activated into order to pass the electrical pulse between the electrodes 24 and ablate the surrounding tissue. The insertion of the electrodes 24 may be performed using the structure 40, or may be performed by hand retraction. Before the procedure is performed, the processor 32 employs software to optimize the insertion sequence using a computational model. Once the tissue has been fully ablated, the electrodes 24 are retracted from the tissue. If desired, the retraction sequence as described in the previous paragraph may be employed at the electrodes 24 are retracted. In FIGS. 9A-9H, the activated electrodes 24 are shown with a darkened tip 44, while the un-activated electrodes 24 are shown with an undarkened tip 44. In FIGS. 10A-10H, the activated electrodes 24 are shown circled and labeled with the reference number 82, with the remainder being un-activated.

Selective activation of the electrodes 24 allows for control of the two-dimensional surface of ablation. Insulating the electrodes 24 with the exception of the uninsulated portion (s) 48 allows for control of the three-dimensional ablation shape. The choice of the array 22 size and activation sequence is determined using prior knowledge of the tumor location, size and shape, typically from imaging information acquired during treatment planning Complex computations based on the fundamental equations governing the physical behavior are used to predict the fields and electroporation effects. Computer algorithms in the processor 32 refine the planned procedure until it is optimized for the given patient anatomy, tumor and desired margin. This optimal set of insertion/retraction or retraction/insertion and electrical activation sequences are then executed on the patient. Thus, the region of ablation is optimally matched to the known and targeted tumor region while sparing surrounding tissue.

While the figures are shown relating to an array 22 having a plurality of rows and columns of electrodes 24, it is to be understood that a single row of electrodes may be used. Also, each row/column in the array 22 does not need to have the same number of electrodes 24.

Preferably, the selection of the electrodes 24 to be activated at the various positions in the tissue to be ablated is driven by the computation models generated by the processor 32, using the information from the medical imaging. The pulsing applied by the pulse generator 26 may be of different magnitudes as the electrodes 24 are being inserted or being refracted from the tissue.

The electroporation apparatus 20 ablates any arbitrary volume of the tissue. The electroporation apparatus 20 provides several advantages. The electroporation apparatus 20 has a sharp ablation margin, relatively low power is required (<1 kV voltage source) to use the electroporation apparatus 20, relatively quick volume ablation (compared to radiofrequency, radiation) is achieved, and the electroporation apparatus 20 does not use ionizing radiation.

As discussed, preferably, the travel of the electrodes is monitored by medical imagery techniques which techniques are known in the art. In addition to, or instead of, such medical imagery techniques, a sensor(s) may be provided on the base plate 36 and/or support plate 38 to measure the travel of the electrodes relative to the support plate 38.

Sensors may be provided to monitor the following parameters, but not limited to, to allow for adaptation and data collection: electrode the electrodes 24, movement of the electrodes 24, bioelectrical impedance, bioelectrical reactance, electrode resistance, electrode contact, and local tissue and electrode temperature. This data can also be utilized as feedback information to allow for the pulse generator 26 to supply the voltage needed to best ablate area 80.

While particular embodiments are illustrated in and described with respect to the drawings, it is envisioned that those skilled in the art may devise various modifications without departing from the spirit and scope of the appended claims. It will therefore be appreciated that the scope of the disclosure and the appended claims is not limited to the specific embodiments illustrated in and discussed with respect to the drawings and that modifications and other embodiments are intended to be included within the scope of the disclosure and appended drawings. Moreover, although the foregoing descriptions and the associated drawings describe example embodiments in the context of certain example combinations of elements and/or functions, it should be appreciated that different combinations of elements and/or functions may be provided by alternative embodiments without departing from the scope of the disclosure and the appended claims.

What is claimed is:

1. An electroporation apparatus comprising:
a pulse generator;
a base plate formed of an insulative material;
a plurality of conductive paths formed on the base plate, each conductive path being electrically connected to the pulse generator for individual electrical actuation by the pulse generator;
a support plate formed of an insulative material;
a first plurality of conductive electrodes affixed to and extending from the base plate, each electrode extending from the base plate and through the support plate at a first nonorthogonal angle, each electrode being electrically connected to a respective conductive path on the base plate to allow individual electrical actuation of the electrodes by the pulse generator, each electrode having a tip, wherein at least one tip extends distally toward a longitudinal axis extending perpendicular to the base plate;
a second plurality of conductive electrodes affixed to and extending from the base plate, each electrode extending from the base plate and through the support plate at a second nonorthogonal angle, each electrode being electrically connected to the respective conductive path on the base plate to allow individual electrical actuation of the electrodes by the pulse generator, each electrode having a tip, wherein at least one tip extends distally toward the longitudinal axis extending perpendicular to the base plate; and
wherein in use, the support plate is held stationary and the base plate and electrodes are moved relative to the support plate to move the electrodes through the support plate from a first position to a second position, such that the tip of each electrode is displaced relative to the support plate while maintaining the angle at which each electrode extends through the support plate, and
wherein in use, certain ones of the electrodes are configured to be activated by the pulse generator when in the first position, and other ones of the electrodes are configured to be activated by the pulse generator when in the second position.

2. The electroporation apparatus of claim 1, wherein the support plate is linear.

3. The electroporation apparatus of claim 1, wherein the support plate is curved.

4. The electroporation apparatus of claim 1, wherein the electrodes are provided in an array.

5. The electroporation apparatus of claim 1, wherein the electrodes are angled relative to each other at an angle greater than 0 degrees.

6. The electroporation apparatus of claim 1, wherein each electrode defines a centerline between opposite ends of the electrode, wherein the centerlines of the first plurality of conductive electrodes are angled in a first similar direction, and wherein the centerlines of the second plurality of conductive electrodes are angled in a second similar direction.

7. The electroporation apparatus of claim 1, wherein the tip of each electrode is sharpened.

8. The electroporation apparatus of claim 1, wherein predetermined ones of the electrodes have a path therethrough to allow infusion of an agent into tissue into which the electrodes are inserted.

9. The electroporation apparatus of claim 1, wherein the electrodes are formed from one of stainless steel, platinum, iridium and gold.

10. The electroporation apparatus of claim 1, further comprising an insulating material provided on at least one portion of each of the electrodes.

11. The electroporation apparatus of claim 10, wherein the insulating material is formed of one of conformal paint, conformal lacquer, and rubber.

12. An electroporation apparatus comprising:
a pulse generator;
a base plate formed of an insulative material;
a plurality of conductive paths formed on the base plate and electrically connected to the pulse generator;
a support plate formed of an insulative material;
a first and second plurality of conductive electrodes provided in an array and affixed and extending from to the base plate, the first plurality of conductive electrodes extending from the base plate and through the support plate at a first nonorthogonal angle and the second plurality of conductive electrodes extending from the base plate and through the support plate at a second nonorthogonal angle, wherein at least one electrode of the first plurality of conductive electrodes extends distally toward a longitudinal axis extending perpendicular to the base plate, and wherein at least one electrode of the second plurality of conductive electrodes extends distally towards the longitudinal axis extending perpendicular to the base plate, each electrode being electrically connected to a respective conductive path on the base plate for individual electrical actuation by the pulse generator, each electrode having insulating material provided on at least one portion thereof, each electrode having a sharpened tip, and predetermined ones of the electrodes have a path therethrough to allow infusion of an agent into tissue into which the electrodes are inserted; and
wherein in use, the support plate is held stationary and the base plate and electrodes are moved relative to the support plate to move the electrodes through the support plate from a first position to a second position, such that the tip of each electrode is displaced relative to the support plate while maintaining the angle at which each electrode extends through the support plate and
wherein in use, certain ones of the electrodes are configured to be activated by the pulse generator when in the first position, and other ones of the electrodes are configured to be activated by the pulse generator when in the second position.

13. The electroporation apparatus of claim 12, wherein the electrodes are angled relative to each other at an angle greater than 0 degrees.

14. The electroporation apparatus of claim 12, wherein each electrode defines a centerline between opposite ends of the electrode, wherein the centerlines of the first plurality of conductive electrodes are angled in a first similar direction, and wherein the centerlines of the second plurality of conductive electrodes are angled in a second similar direction.

15. The electroporation apparatus of claim 12, wherein the electrodes are formed from one of stainless steel, platinum, iridium and gold.

16. The electroporation apparatus of claim 12, wherein the insulating material is formed of one of conformal paint, conformal lacquer, and rubber.

17. An electroporation apparatus comprising:
a pulse generator including a processor;
a base plate formed of an insulative material;
a plurality of conductive paths formed on the base plate electrically connected to the pulse generator for electrical actuation by the pulse generator;
a support plate formed of an insulative material;
a first and a second plurality of conductive electrodes affixed to and extending from the base plate the first plurality of conductive electrodes extending from the base plate and through the support plate at a first nonorthogonal angle and the second plurality of conductive electrodes extending from the base plate and through the support plate at a second nonorthogonal angle, wherein at least one electrode of the first plurality of conductive electrodes extends distally toward a longitudinal axis extending perpendicular to the base plate, and wherein at least one electrode of the second plurality of conductive electrodes extends distally toward the longitudinal axis extending perpendicular to the base plate, each electrode being electrically connected to a respective conductive path on the base plate to allow individual electrical actuation of the electrodes by the pulse generator, each electrode having a tip;
connecting structure connecting the base plate and the support plate together, the connecting structure configured to cause movement of the base plate relative to the support plate, wherein activation of the connecting structure is controlled by the processor,
wherein in use, the support plate is held stationary and the base plate and electrodes are moved relative to the support plate to move the electrodes through the support plate such that the tip of each electrode is displaced relative to the support plate while maintaining the angle at which each electrode extends through the support plate.

18. The electroporation apparatus of claim 17, wherein the electrodes are provided in an array.

19. The electroporation apparatus of claim 17, wherein predetermined ones of the electrodes have a path therethrough to allow infusion of an agent into tissue into which the electrodes are inserted.

20. The electroporation apparatus of claim 17, further comprising an insulating material provided on at least one portion of each of the electrodes.

* * * * *